United States Patent [19]
Satzinger et al.

[11] 3,971,794
[45] July 27, 1976

[54] THIAZOLIDINONE ACETIC ACID DERIVATIVES

[75] Inventors: Gerhard Satzinger, Denzlingen; Manfred Herrmann, St. Peter; Karl-Otto Vollmer, Freiburg, all of Germany

[73] Assignee: Warner-Lambert Company, Morris Plains, N.J.

[22] Filed: Feb. 27, 1975

[21] Appl. No.: 553,715

[30] Foreign Application Priority Data
Mar. 25, 1974 Germany............................ 2414345

[52] U.S. Cl............................. 260/293.68; 424/267
[51] Int. Cl.[2]........................................ C07D 295/12
[58] Field of Search............................... 260/293.68

[56] References Cited
UNITED STATES PATENTS

| | | | |
|---|---|---|---|
| 3,064,003 | 11/1962 | Satzinger...................... | 260/306.7 R |
| 3,072,653 | 1/1963 | Satzinger ...................... | 260/293.68 |

OTHER PUBLICATIONS

Heidenreich et al., Arzneimittel Forsch 14 : 1242–1248 (1964).

*Primary Examiner*—Sherman D. Winters
*Attorney, Agent, or Firm*—Albert H. Graddis; Frank S. Chow; George M. Yahwak

[57] ABSTRACT

The present invention relates to novel thiazolidinone acetic acid derivatives and their preparation. These derivatives show diuretic properties when used as pharmaceuticals.

8 Claims, No Drawings

THIAZOLIDINONE ACETIC ACID DERIVATIVES

The new thiazolidinone-acetic acid derivatives according to the present invention are compounds of the general formula:

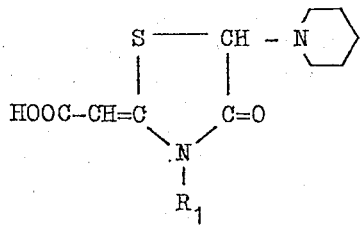

wherein $R_1$ is a lower alkyl radical; and the pharmacologically compatible salts thereof.

U.S. Pat. Nos. 3,182,063 and 3,072,653, as well as Liebigs Annalen der Chemie, 665, 150–165/1963, describe certain substituted 2-methylene-thiazolidin-4-ones which have an analgesic, sedative and antiinflammatory action. Some halogen-substituted compounds of this type are also known to possess a certain gall stimulating and diuretic action. These previously known biologically active compounds differ from the novel compounds by the absence of a free carboxyl group.

It is known that 3-methyl analogues of compounds unsubstituted in the 5-position and having a free carboxyl group can be prepared by the gentle saponification of the corresponding ethyl ester. Attempts to prepare, in this manner, compounds of general formula I which possess a basic substituent in the 5-position proved to be unsuccessful and, in every case, resulted in an isomerization or a destruction of the ring system. This was expected since these compounds simultaneously have the structure of cyclic enamine carbonyl compounds, of ketene-S,N-acetals, and of thioaminals. The reactivity and sensitivity of such groupings to alkaline and acidic influences is generally known from the literature (see Liebigs Ann. d. Chemie, 725, 66–68/1969).

We have now found that acid-catalysed alkyl-oxygen splitting is possible when an ester of the general formula:

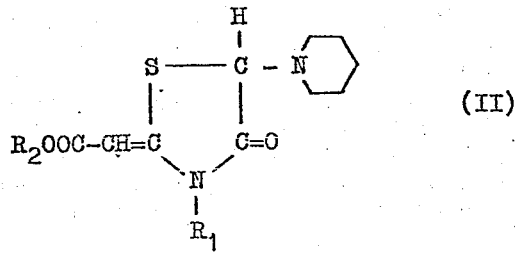

(II)

wherein $R_1$ has the same meaning as above and $R_2$ is an alkyl radical with 2–6 carbon atoms, is treated at a low temperature with an approximately 40% to 50% solution of hydrogen bromide in acetic acid and the free amine acid (I), after removal of the acid mixture, is isolated. The range of the solution being limited mainly by the solubility of HBr in the acid. Although acetic acid is preferred, lower alkyl acids of 1 to 5 carbons, such as propionic or butyric acids, may also be used.

Under these conditions, the alkyl radical $R_2$ is gently split off as an alkene or an alkyl bromide. In spite of the high acid concentration, neither isomerisation nor destruction nor the expected decarboxylation of the free acid formed takes place.

The radicals $R_1$ are straight-chained or branched alkyl radicals with up to 4 carbon atoms, and include methyl, ethyl, n-propyl, isopropyl, n-butyl, isobutyl and tert.-butyl radicals.

As pharmacologically compatible salts, there are the alkali metal salts, especially the potassium salts, as well as the alkaline earth metal salts. These can be prepared by reacting the free amino acids (I) with appropriate metal hydroxides or carbonates.

The alkyl-oxygen splitting, according to the present invention is carried out in such a manner that the compounds of general formula (II) are introduced, at a temperature of −5°C. to +5°C, into a 40% solution of hydrogen bromide in glacial acetic acid, and the splitting off of the alkyl radical is initiated by slowly warming the reaction mixture at ambient temperature, i.e. to about 15°–25°C. After completion of the reaction, which takes about 1 to 70 hours, the acid mixture is removed in a vacuum and the residue digested with water. The free amino acids (I) can then be precipitated out at pH 6 and isolated.

From thermodynamic reasons the acids of the invention prefer the HOOC/N-$R_1$ trans-configuration with regard to the exocyclic double bond ("Z"-configuration).

If the free acids are subsequently to be converted to their potassium salts, then the compounds (I) can be introduced into an equimolar amount of aqueous potassium bicarbonate or potassium carbonate solution, which contains 1–15% of a lower alcohol, at a temperature of about 40°–60°C. and the salt isolated by drying, preferably freeze drying.

Compounds of general formula (II) used as starting materials are known or can be prepared in a manner analogous to that used for the preparation of the known compounds, by reacting the compounds described in U.S. Pat. No. 3,072,653 with piperidine.

The compounds of general formula I possess valuable pharmacological activities, especially a diuretic activity, and are characterized by an interesting spectrum of activity not previously known for diuretic compounds. Furthermore, the outstanding water solubility of the alkali metal salts at a physiologically optimum pH value permits a wide field of use, especially in the therapy of acute lung and brain edema and in the treatment of acute kidney failure; it is also possible to increase the flow of blood through the kidneys by 30–50%, without reducing the filtration rate, whereas previously known diuretics do not substantially influence the flow of blood through the kidneys. Furthermore, the known diuretics in contradistinction to the compounds of the present invention, reduce the filtration rate.

As animal experiments on dogs have shown, the compounds according to the present invention in contradistinction to the commercially available diuretics, in the case of experimentally equally adjusted diuresis, the excretion of potassium is scarcely influenced. Furthermore, the new compounds (I) have a remarkably low toxicity and, besides their diuretic action, also exhibit an outstanding antihypertensive effect. In addition, a regulatory effect on the body temperature has been observed.

The new compounds of general formula I according to the present invention, as well as their pharmacologically compatible salts, can be administered enterally or parenterally, which the ester cannot, in admixture with liquid or conventional solid pharmaceutical diluents or carriers. As injection medium, it is particularly preferred to use water which contains the conventional additives for injection solutions, for example, stabilizing agents, solubilizing agents and/or buffers. Compositions suitable for oral administration can, if desired, contain flavoring and/or sweetening agents.

The dosage depends upon the nature and severity of the disease to be treated. The individual oral dose lies between 10 and 500 mg. and the subcutaneously or intravenously administered individual dose can be between about 5 to 200 mg.

The following Examples are given for the purpose of illustrating the present invention:

EXAMPLE 1

3-Methyl-4-oxo-5N-piperidino-thiazolidin-2-ylidene-acetic acid

Variant A 55 g. butyl 3-methyl-4-oxo-5N-piperidino-thiazolidin-2-ylidene-acetate is introduced, at −3° to 0°C., into 100 cc. of a 40% solution of hydrogen bromide in acetic acid. The reaction mixture is slowly warmed to 20°C. and then left at this temperature for 1.5 hours. Subsequently, the greater part of the hydrogen bromide-acetic acid phase is removed under waterpump vacuum at a bath temperature of 25°–40°C. The residue is digested with 0.5 liter water, and the pH adjusted to 6.0 with sodium bicarbonate. Foaming can be inhibited by the addition of ether. The solid product is filtered off with suction and dried in a vacuum over anhydrous calcium chloride. Any remaining starting material can easily be separated by dissolving in cold 2N aqueous sodium carbonate solution, filtering and acidifying the filtrate with dilute acetic acid. There is obtained 25 g. (56% of theory) 3-methyl-4-oxo-5N-piperidino-thiazolidin-2-ylidene-acetic acid which melts, with decomposition, at 163.9°C., after recrystallization from methanol or ethanol.

Analysis: $C_{11}H_{16}N_2O_3S$ (M.W. 256.32); calc.: C 51.54%; H 6.29%; N 10.93%; S 12.51%; found: 51.67%; 6.12%; 10.77%; 12.34%.

The butyl 3-methyl-4-oxo-5N-piperidino-thiazolidin-2-ylidene-acetate used as starting material is prepared as follows:

141 g. ethyl tert.-butyl-cyanoacetate (b.p. 60°C./1.5 mm.Hg.; $n^{20}$ 1.4180) and 120 cc. ethyl thioglycolate are dissolved in 1 liter benzene, mixed with 140 cc. triethylamine and stirred for 72 hours at ambient temperature. The bulk of the solvent is then distilled off in a vacuum and the solid residue is separated and washed with a little benzene on a suction filter. There is obtained, after air drying, 134 g. (79% of theory) tert.-butyl 4-oxo-thiazolidin-2-ylidene-acetate which, after recrystallization from isopropanol, melts at 177.4°C.

63.5 g. tert.-butyl 4-oxo-thiazolidin-2-ylidene-acetate and 41.4 g. potassium carbonate are suspended in 250 cc. methanol. The reaction mixture is heated to reflux temperature and mixed dropwise with a solution of 37.8 g. dimethyl sulphate in 50 cc. methanol. After an hour, the reaction is finished. The solvent is removed in a vacuum and the residue introduced into 0.5 liter water. The crude tert.-butyl 3-methyl-4-oxo-thiazolidin-2-ylidene-acetate is taken up in ether and the ethereal phase is then dried and evaporated. The residue is recrystallized from cyclohexane. There is obtained 56 g. (82% of theory) tert.-butyl (3-methyl-4-oxo-thiazolidin-2-ylidene)-acetate, which melts at 77.4°C.

36.8 g. tert.-butyl 3-methyl-4-oxo-thiazolidin-2-ylidene-acetate is dissolved in 700 cc. anhydrous carbon tetrachloride. Under reflux conditions, there is first introduced 0.3 g. azo-bis-isobutyric acid nitrile and then, within a period of 10 minutes, 29 g. N-bromosuccinimide. After boiling under reflux for 20 minutes, the reaction mixture is filtered and the filtrate is evaporated to dryness in a vacuum. The oily residue is taken up in 0.5 liter benzene, cooled to +5°C. and mixed in several portions with 32 cc. piperidine. After standing for several hours at ambient temperature, the piperidine hydrobromide formed is separated off and the filtrate evaporated in a vacuum. After the addition of 50 cc. isopropanol, the mixture is cooled to 0°C. The precipitated tert.-butyl 3-methyl-4-oxo-5N-piperidino-thiazolidin-2-ylidene-acetate is recrystallized from isopropanol. The yield is 21.5 g. (38% of theory over 2 stages) and the product melts at 154°C.

Analysis: $C_{15}H_{24}N_2O_3S$ (M.W. 312.41); calc.: C 57.66%; H 7.74%; N 8.97%; S 10.26%; found: 57.56%; 7.80%; 9.15%; 10.33%.

Variant B 100 g. ethyl 3-methyl-4-oxo-5N-piperidino-thiazolidin-2-ylidene-acetate is introduced, while stirring at 0°C., into 200 cc. of a 40% solution of hydrogen bromide in acetic acid. The vessel containing the reaction mixture is closed with a Bunsen valve (in order to avoid an overpressure of ethylene) and the reaction mixture stirred with a magnetic stirrer for 65 hours at ambient temperature. The reaction mixture is then worked up in the manner described in Variant A. There is obtained 47.0 g. (53% of theory) 3-methyl-4-oxo-5N-piperidino-thiazolidin-2-ylidene-acetic acid which melts, with decomposition, at 163.9°C.

EXAMPLE 2

Potassium 3-methyl-4-oxo-5N-piperidino-thiazolidin-2-ylidene-acetate 5.1 g. (0.02 mol) 3-methyl-4-oxo-5N-piperidino-thiazolidin-2-ylidene-acetic acid is pasted with 10% ethanol and digested with 50 ml. of a 4% aqueous solution of potassium bicarbonate. The mixture is briefly heated on a water-bath to 50°C. until gas evolution is complete and complete solution is obtained. The mixture is then cooled to 15°–20°C. and water removed in a rotary evaporator at 0.05 mm.Hg. pressure under freeze drying conditions. The residue is recrystallized from isopropanol. There is obtained 3.5 g. (59.3% of theory) of potassium 3-methyl-4-oxo-4N-piperidino-thiazolidin-2-ylidene-acetate in the form of colorless crystals which decompose at 150°C.

EXAMPLE 3

3-Ethyl-4-oxo-5N-piperidino-thiazolidin-2-ylidene-acetic acid 50 g. ethyl 3-ethyl-4-oxo-5N-piperidino-thiazolidin-2-ylidene-acetate is reacted and worked up in a manner analogous to that described in Example 1. There is obtained 12.5 g. (28% of theory) 3-ethyl-4-oxo-5N-piperidino-thiazolidin-3-ylidene-acetic acid which, after recrystallization from methanol, melts at 148°C. (Melting takes place with decarboxylation and is somewhat dependent upon the rate of heating up).

Analysis: $C_{12}H_{18}N_2O_3S$ (M.W. 270.35); calc.: C 53.31%; H 6.71%; N 10.36%; S 11.86%; found: 53.41%; 6.59%; 10.19%; 11.72%.

The following compounds are prepared in an analogous manner:

3-propyl-4-oxo-5N-piperidino-thiazolidin-2-ylidene-acetic acid;
3-n-butyl-4-oxo-5N-piperidino-thiazolidin-2-ylidene-acetic acid;
3-isobutyl-4-oxo-5N-piperidino-thiazolidin-2-ylidene-acetic acid.

EXAMPLE 4

20 g. of ethyl 3-methyl-4-oxo-5N-piperidino-thiazolidin-2-ylidene-acetate is introduced, while stirring at 0°–5°C. into 50 cc. of a 40% solution of hydrogen bromide in propionic acid. The solution is processed as described under Example 1, Variant B; reaction time 72 hours. Yield 7.0 g (39% of theory). M.p. (decomp.) 163°C.

EXAMPLE 5

20 g. of ethyl 3-methyl-4-oxo-5N-piperidino-thiazolidone-2-ylidene-acetate is introduced, while stirring at 0°–5°C. into 50 cc. of a 40% solution of hydrogen bromide in butyric acid. The solution is processed as described under Example 1, Variant B; reaction time 70 hours. Yield 6.9 g (39% of theory). M.p. (decomp.) 163°–4°C.

Compounds of the present invention exhibit marked pharmaceutical advantages when compared to the known ethyl-3-methyl-4-oxo-5-piperidino-$\Delta^{2,\alpha}$-thiazolidineacetate of U.S. Pat. No. 3,072,653.

Compounds of the present invention are available for injection and can therefore be used in medical emergencies such as acute lung and brain edema. Compounds of the present invention are more potent than the thiazolidineacetate after intragastric and intravenous administration. Compounds of the present invention have little effect on potassium excretion, even less than with the commercially available Furosemide which is known to have little effect on potassium excretion.

The following examples illustrate the improved activities of the present compounds when compared to previously known compounds. Etozolin refers to ethyl-3-methyl-4-oxo-5-piperidino-$\Delta^{2,\alpha}$-thiazolidineacetate; 3282 refers to 3-methyl-4-oxo-5N-piperidino-thiazolidine-acetic acid.

EXAMPLE 6

DIURESIS

1. Experiments by intragastric administration method

Experiments were carried out in 5 unanesthetized adult female Beagle dogs, weighing 15 to 22 kg, which were trained to lie on a table without fixation. The animals were not episiotomized. A rubber catheter was introduced into the bladder and excreted urine was collected separately for each animal and the volume measured in 30 minute intervals. After a constant urine flow was achieved, test substances were administered by stomach tube. The diuretics were diluted with saline solution so that a constant volume of 25 ml/kg was reached. Three animals received the test substances and two served as controls. The lowest dose of the diuretics administered was 1.56 mg/kg. Dosages were increased by a factor of 2 up to 50 mg/kg.

Results

Table 1

Comparison of the maximal achievable effects of Etozolin and 3282 on the diuresis of conscious dogs after intragastric administration.

| Substance | Dose mg/kg | ml/animal/min |
|---|---|---|
| Etozolin | 25.0 | 7.8 |
| 3282 | 25.0 | 10.9 |

As can be seen from table I the maximal diuretic effect of both substances is reached after 25.0 mg/kg. An increase of the dose does not result in a further increase of urine excretion. The maximal achievable effect of 3282, however, is by far higher than that of Etozolin.

2. Experiments by intravenous administration method

Experiments were performed in male and female mongrel dogs, anesthetized with pentobarbital. The body weight was between 9 and 11 kg. After laparotomy the proximal part of the ureters was canulated and the urine excreted by each kidney collected in periods of 10 minutes. Arterial and venous pressure were recorded throughout the experiment. At the beginning 1.5 ml/kg. min. of a tempered saline solution were infused for one and a half hour. After constant urine-flow was reached, the diuretics were injected into the femoral vein. The initial dose was 2.0 mg/kg which was increased with the factor 2 up to 64.0 mg/kg. Two animals were used for each dose level.

The results obtained showed that there is a straight dose dependent effect after administration of 3282 ($r = 0.8799$). Following 32.0 mg/kg the urinary excretion is increased to 16 ml/minute per animal. The dose dependency is less significant in the case of Etozolin ($r = 0.5583$), this substance being far less active: following administration of 32.0 mg/kg urinary flow is only increased to 2.25 ml/minute per animal.

EXAMPLE 7

Influence on potassium excretion
method

A total of 19 clearance experiments in 8 female and 1 male dogs, weighing from 17 to 25 kg, were done. Animals were anesthetized by 30.0 mg/kg pentobarbital intravenously.

At the beginning of the experiment one liter saline solution was infused within one hour. In the urine which was collected by using a bladder catheter besides other parameters potassium and sodium concentrations were determined by flame photometry.

The results obtained showed that with higher amounts of sodium excreted, potassium excretion is by far more increased with Furosemide than with 3282.

EXAMPLE 8

Acute Toxicity

The acute toxicity of 3282 is very favorable.

In experiments in rats in which 3282 was injected into the tail vein, no deaths were seen up to dosages of 1,000 mg/kg (higher dosages were not used). Thus the intravenous toxicity of 3282 is by far more favorable than that of Etozolin. The LD$_{50}$ of Etozolin in rats is 56.6 mg/kg i.v. (confidence limits: 45.9 – 69.5 mg/kg).

In experiments in mice in which 3282 was administered intragastrically as aqueous solution, none of the animals died up to dosages of 2,250 mg/kg within 48 hours.

Having thus described our invention in such clear, concise, and exact terms to allow one skilled in the art to make and use the same, we claim:

1. A thiazolidinone-acetic acid derivative of the formula:

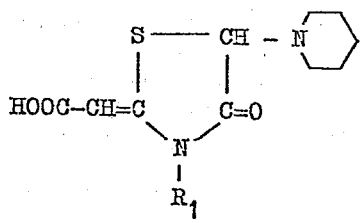

wherein $R_1$ is a lower alkyl radical containing 1 to 4 carbon atoms or a physiologically compatible salt thereof.

2. A derivative according to claim 1 wherein $R_1$ is methyl and which is 3-Methyl-4-oxo-5N-piperidino-thiazolidin-2-ylidene-acetic acid.

3. A derivative according to claim 1 wherein $R_1$ is methyl and which is Potassium 3-methyl-4-oxo-5N-piperidino-thiazolidin-2-ylidene-acetate.

4. A derivative according to claim 1 wherein $R_1$ is ethyl and which is 3-Ethyl-4-oxo-5N-piperidino-thiazolidin-2-ylidene-acetic acid.

5. A derivative according to claim 1 wherein $R_1$ is n-propyl and which is 3-n-Propyl-4-oxo-5N-piperidino-thiazolidin-2-ylidene-acetic acid.

6. A derivative according to claim 1 wherein $R_1$ is n-butyl and which is 3-n-Butyl-4-oxo-5N-piperidino-thiazolidin-2-ylidene-acetic acid.

7. A derivative according to claim 1 wherein $R_1$ is isobutyl and which is 3-Isobutyl-4-oxo-5N-piperidino-thiazolidin-2-ylidene-acetic acid.

8. A derivative according to claim 1 which is 3-isopropyl-4-oxo-5N-piperidino-thiazolidin-2-ylidene-acetic acid.

* * * * *